United States Patent [19]

Yokoshima et al.

[11] Patent Number: 4,647,638
[45] Date of Patent: Mar. 3, 1987

[54] NOVEL ORGANOPHOSPHATE AND ADHESIVE COMPRISING IT

[75] Inventors: Minoru Yokoshima, Yamaguchi; Tetsuo Ohkubo, Ube, both of Japan

[73] Assignee: Nippon Kayaku Kabushiki Kaisha, Tokyo, Japan

[21] Appl. No.: 798,916

[22] Filed: Nov. 18, 1985

Related U.S. Application Data

[62] Division of Ser. No. 728,944, Apr. 30, 1985, Pat. No. 4,581,180.

[30] Foreign Application Priority Data

Feb. 22, 1985 [JP] Japan .................................. 60-32801

[51] Int. Cl.$^4$ ...................... C09S 3/00; C08F 130/02; A62D 3/00
[52] U.S. Cl. .................... 526/277; 523/176; 252/186.42
[58] Field of Search ................ 526/278, 277; 523/176; 252/186.42

[56] References Cited

U.S. PATENT DOCUMENTS 4,322,509 3/1982 Zalucha .............................. 525/287

FOREIGN PATENT DOCUMENTS 59-141588 8/1984 Japan .

OTHER PUBLICATIONS

Chem. Abstract vol. 102, entry 46139e.

Primary Examiner—Edward J. Smith
Assistant Examiner—Peter F. Kulkosky
Attorney, Agent, or Firm—Henry C. Nields

[57] ABSTRACT

Novel organophosphates of the general formula:

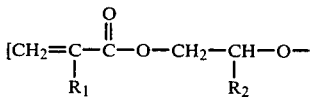

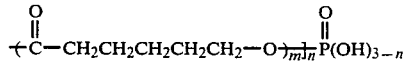

wherein $R_1$ and $R_2$ each represents H or $CH_3$, m is a numeral of 1–5 and n is a numeral of 1–2, and adhesives comprising them.

4 Claims, No Drawings

NOVEL ORGANOPHOSPHATE AND ADHESIVE COMPRISING IT

This application is a division of application Ser. No. 728,944, filed Apr. 30, 1985, and now U.S. Pat. No. 4,581,180.

DETAILED DESCRIPTION OF THE INVENTION

This invention relates to novel organophosphates and adhesives comprising them.

Anaerobically setting adhesives are adhesives which remain liquid as long as they are in contact with air or oxygen but, upon being shut off from air or oxygen, rapidly polymerize and set. By utilizing such a feature, they are widely employed as lossening prevention agents for bolts and nuts, sealants for piping parts, flange parts etc., leakproofing agents for high pressure or high temperature liquids or gases, etc.

As such anaerobically setting adhesives, a wide variety of adhesives have heretofore been known. For example, there are anaerobically setting adhesives comprised of a polymerizable monomer such as 2,2-bis(4-methacryloxydiethoxyphenyl)propane etc., with bis(2-hydroxyethyl methacrylate)phosphate or 2-hydroxyethyl methacrylate phosphate and an organic peroxide disclosed in U.S. Pat. No. 4,044,044. Although they have relatively good adhesion and also good setting properties, the essential component in the aforesaid compositions, i.e., bis(2-hydroxy ethyl methacrylate)phosphate or 2-hydroxyethyl methacrylate phosphate, has great toxicity to the skin and hence handling thereof causes a problem in preparing a composition, and if the adhesive pressed out of the site to be bonded remains without being set, it can cause rash when contacted with the skin.

This invention relates to novel organophosphates which have overcome the above-described drawbacks, and to anaerobically setting adhesives comprising them.

Accordingly, this invention relates to a novel organophosphate of the following formula [II]:

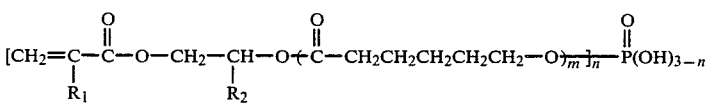

wherein $R_1$ and $R_2$ each represents H or $CH_3$, m is a numeral of 1-5, preferably 1-2, and n is a numeral of 1-2.

Further, this invention also relates to an adhesive which is characterized by comprising an anaerobically polymerizable monomer (A), a phosphate of the aforesaid formula [II] (B) and an organic peroxide (C).

The phosphate of the aforesaid formula [II] may be produced by esterifying a compound of the following formula [I]:

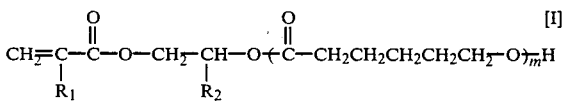

wherein $R_1$ and $R_2$ each represents H or $CH_3$ and m is a numeral of 1-5 with phosphoric anhydride.

To describe in more detail, the compound of the formula [I] is that obtained by condensation of a hydroxyalkyl acrylate or methacrylate with epsilon-caprolactone. Therefore, the m in the formula [I] is the average number of the epsilon-caprolactone added. The process of its production is disclosed in Japanese Patent Application Laid-open No. 185236/1982.

Where the compound of the formula [I] is esterified with phosphoric anhydride, the phosphoric anhydride is used in an amount of 0.5-1.5 moles per 3 moles of the compound of the formula [I], preferably 0.95-1.05 moles, and particularly preferably 1 mole. By controlling the ratio of the compound of the formula [I] to the phosphoric anhydride used, the value n may be appropriately adjusted.

The reaction may be easily proceeded by slowing adding phosphoric anhydride to the compound of the formula [I]. If necessary, an organic solvent inert to the reaction may be used, e.g., benzene, cyclohexane, toluene etc. The reaction temperature may be suitably in the range of 0°-100° C., advantageously at 30°-70° C. in view of a cut in reaction time and prevention of polymerization. Said reaction is preferably effected in the presence of a polymerization inhibitor in order to minimize or retard polymerization of acrylic double bonds. The aforesaid polymerization inhibitor is known in the art, and is preferably used at a concentration of 0.01-1% by weight based on said reaction mixture. Examples of such a polymerization inhibitor include hydroquinone, p-methoxyphenol, 2,4-dimethyl-6-t-butylphenol, p-benzoquinone etc.

The adhesives comprising the above-described component (A), component (B) and component (C) of this invention are now described.

The anaerobically polymerizable monomer (A) is preferably an acrylate or methacrylate compound, and specific examples thereof include 2-hydroxyethyl methacrylate, 2-hydroxypropyl methacrylate, 2-hydroxyethyl acrylate, polyethylene glycol dimethacrylate, trimethylolpropane trimethacrylate, 2,2-bis(4-methacryloxydiethoxyphenyl)propane, 2,2-bis(4-methacryloxytriethoxyphenyl)propane and the like monomers. These polymeric monomers may be used either alone or as a mixture of two or more thereof at any proportion.

As the phosphate of the formula [II], an ester of the formula [II] wherein $R_1$ represents $CH_3$, $R_2$ represents H and m represents a value of 1-2 is particularly preferred.

The organic peroxide (C) acts as a polymerization initiator, and examples of such a substance include benzoyl peroxide, methyl ethyl ketone peroxide, cyclohexane peroxide, cumene hydroperoxide, di-t-butyl peroxide, lauroyl peroxide, dicumyl peroxide etc. The adhesives of this invention may be obtained by uniformly mixing the above-described polymerizable monomer (A), phosphate (B) and organic peroxide (C).

The amount of the component (B) per 100 parts by weight of the component (A) used in the compositions of this invention is preferably 0.05-30 parts by weight, particularly preferably 0.3-10 parts by weight. If the amount of the component (B) is less than 0.05 part by weight, the adhesive force will not be strong enough, whereas if it is used in an amount of more than 30 parts by weight, the cost of the composition is merely increased.

The organic peroxide (C) is preferably used in an amount of 0.2–3 parts by weight per 100 parts by weight of the total of the above-described component (A) and the component (B).

In addition to the above-described components, it is also possible to add and mix an appropriate amount of a polymerization accelerator in the adhesives of this invention in order to further facilitate polymerization and setting. As the polymerization accelerator, for example, o-sulfobenzoicimide, 1,2,3,4-tetrahydroquinoline, dextrin, etc. are used, and their amount used is preferably 0.1–2 parts by weight per 100 parts by weight of the monomer mixture.

Applications of the adhesives of this invention are, for example, for fitting of bolts and nuts, sealing of piping parts and flange parts, bonding of metals such as iron, copper, chromium, nickel etc., e.g., bonding of iron plates etc., and the like. The adhesives of this invention set at normal temperature to elevated temperatures (for example, 50°–150° C.).

The adhesives of this invention utilize the component (B), namely, the phosphate of the formula [II], and therefore have greater adhesive force than the conventional adhesives.

The phosphates of the formula [II] of this invention have only low levels of skin toxicity and hence their handling is safe. Further, the phosphates of the formula [II] are free from strong odors and thus also are advantageous in this point.

The phosphates of the formula [II] of this invention are not only used as one component for adhesives but also useful as adhesion improvers for paint and ink compositions for metals, in which case, the phosphate forms a homopolymer or copolymer by an appropriate polymerization initiating method, for example, by addition of an organic peroxide, irradiation with ultraviolet light or electron ray, etc.

This invention is more particularly described by the following examples, wherein the parts are parts by weight.

EXAMPLE 1

A one-liter reactor equipped with a stirrer, a temperature controlling device, a thermometer and a condenser was charged with 439.2 parts of a compound of the following formula:

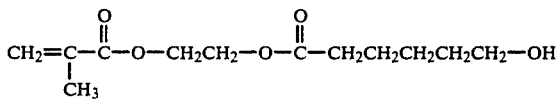

which was a condensation product of 1 mole of 2-hydroxyethyl methacrylate and 1 mole of epsilon-caprolactone and 0.131 part of hydroquinone monomethyl ester, then 85.17 parts of phosphoric anhydride was gradually added to the reaction mixture while maintaining the temperature of the reaction mixture at 40°–60° C. and, upon the completion of addition, the reaction was continued for 2 hours while maintaining the temperature of the reaction mixture at 50° C. to obtain 524 parts of a viscous pale yellow liquid. This had the following properties. The n value was about 1.5.

| Specific Gravity (25° C.) | 1.1940 | | |
|---|---|---|---|
| Viscosity (25° C.) | 558.0 CPS | | |
| Acid Value | 218.3 mg KOH/g | | |
| Refractive Index (20° C.) | 1.4650 | | |
| Elementary Analysis: | C (%) | H (%) | P (%) |
| | 49.21 | 6.89 | 7.03 |

The absorbed frequencies of the obtained product were measured by highly resolving nuclear magnetic resonance (NMR) and the results are shown below.

| No. | Absorbed Frequency (Hz) |
|---|---|
| 1 | 2710.937 |
| 2 | 2646.484 |
| 3 | 2638.671 |
| 4 | 2601.562 |
| 5 | 2556.640 |
| 6 | 2554.687 |
| 7 | 2550.781 |
| 8 | 2546.875 |
| 9 | 2082.031 |
| 10 | 2076.171 |
| 11 | 1943.359 |
| 12 | 1929.687 |
| 13 | 1917.968 |
| 14 | 1226.562 |
| 15 | 1193.359 |
| 16 | 1162.109 |
| 17 | 1128.906 |
| 18 | 1070.312 |
| 19 | 1044.921 |
| 20 | 1039.062 |
| 21 | 1023.437 |
| 22 | 1017.578 |
| 23 | 1009.765 |
| 24 | 998.046 |
| 25 | 992.187 |
| 26 | 984.375 |
| 27 | 970.703 |
| 28 | 966.796 |
| 29 | 945.312 |
| 30 | 568.359 |
| 31 | 544.921 |
| 32 | 505.859 |
| 33 | 482.421 |
| 34 | 474.609 |
| 35 | 457.031 |
| 36 | 416.015 |
| 37 | 406.250 |
| 38 | 400.390 |
| 39 | 335.937 |
| 40 | 306.640 |

For the above measurement, tetramethylsilane was used as a standard substance, chloroform was used as a solvent, and the measurement was conducted first by $H^1$ and $C^{13}$—H coupling and finally by $C^{13}$—D coupling to obtain identification results. Of the above-described absorptions, No. 15, 16 and 17 indicate the peak positions of the solvent.

EXAMPLE 2

The same reactor as in Example 1 was charged with 429.6 parts of a compound of the following formula:

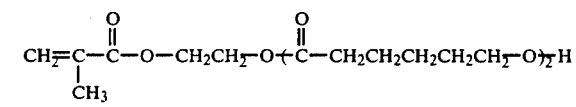

which was a condensation product of 1 mole of 2-hydroxyethyl methacrylate and 2 moles of epsilon-caprolactone and 0.12 part of hydroquinone monomethyl ether, followed by addition of 56.78 parts of phosphoric anhydride in a manner similar to that in Example 1, and the reaction was continued for 2 hours while maintaining the reaction temperature at 50° C. to obtain 486 parts of a viscous pale yellow liquid. This had the following properties. The n value was about 1.5.

| Specific Gravity (25° C.) | 1.1660 | | |
|---|---|---|---|
| Viscosity (25° C.) | 1358.4 CPS | | |
| Acid Value | 125.8 mg KOH/g | | |
| Refractive Index | 1.4700 (20° C.) | | |
| Elementary Analysis: | C (%) | H (%) | P (%) |
| | 52.89 | 7.45 | 5.02 |

| Results of NMR Measurement | |
|---|---|
| No. | Absorbed Frequency (Hz) |
| 1 | 2609.375 |
| 2 | 2605.468 |
| 3 | 2599.609 |
| 4 | 2507.812 |
| 5 | 2037.109 |
| 6 | 1894.531 |
| 7 | 1890.625 |
| 8 | 1878.906 |
| 9 | 1718.750 |
| 10 | 1189.453 |
| 11 | 1158.203 |
| 12 | 1125.000 |
| 13 | 1033.203 |
| 14 | 1011.718 |
| 15 | 1007.812 |
| 16 | 1001.953 |
| 17 | 986.328 |
| 18 | 960.937 |
| 19 | 953.125 |
| 20 | 933.593 |
| 21 | 927.734 |
| 22 | 507.812 |
| 23 | 503.906 |
| 24 | 445.312 |
| 25 | 439.453 |
| 26 | 419.921 |
| 27 | 378.906 |
| 28 | 369.140 |
| 29 | 363.281 |
| 30 | 269.531 |

Of the above absorptions, No. 10, 11 and 12 indicate the peak positions of the solvent.

EXAMPLE 3

The same reactor as in Example 1 was charged with 443.8 parts of a compound of the following formula:

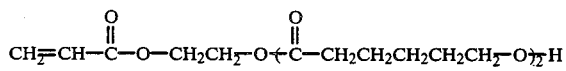

which was a condensation product of 1 mole of 2-hydroxyethyl acrylate and 2 moles of epsilon-caprolactone and 0.25 part of hydroquinone monomethyl ether, followed by addition of 61.0 parts of phosphoric anhydride in a manner similar to that in Example 1, and the reaction was continued for 2 hour while maintaining the reaction temperature at 50° C. to obtain 504 parts of a viscous pale yellow liquid. This had the following properties. The n value was about 1.5.

| Specific Gravity (25° C.) | 1.1860 | | |
|---|---|---|---|
| Viscosity (25° C.) | 2090 CPS | | |
| Acid Value | 130.0 mg KOH/g | | |
| Refractive Index | 1.4730 (20° C.) | | |
| Elementary Analysis: | C (%) | H (%) | P (%) |
| | 51.98 | 7.18 | 5.26 |

| Results of NMR Measurement | |
|---|---|
| No. | Absorbed Frequency (Hz) |
| 1 | 2605.468 |
| 2 | 2599.609 |
| 3 | 2572.265 |
| 4 | 2492.187 |
| 5 | 2488.281 |
| 6 | 1970.703 |
| 7 | 1958.984 |
| 8 | 1927.734 |
| 9 | 1917.968 |
| 10 | 1718.750 |
| 11 | 1189.453 |
| 12 | 1158.203 |
| 13 | 1125.000 |
| 14 | 1060.546 |
| 15 | 1009.765 |
| 16 | 1003.906 |
| 17 | 986.328 |
| 18 | 958.984 |
| 19 | 951.171 |
| 20 | 931.640 |
| 21 | 927.734 |
| 22 | 519.531 |
| 23 | 507.812 |
| 24 | 503.906 |
| 25 | 445.312 |
| 26 | 439.453 |
| 27 | 419.921 |
| 28 | 378.906 |
| 29 | 369.140 |
| 30 | 363.281 |

Of the above absorptions, No. 11, 12 and 13 indicate the peak positions of the solvent.

APPLICATION EXAMPLES 1, 2 AND 3 AND COMPARATIVE EXAMPLE 1

To 5 parts of the novel organic phosphates obtained in Examples 1-3 respectively were added 40 parts of a diacrylate obtained by esterifying an ethylene oxide (4 moles) addition product of bisphenol A with 2 moles of acrylic acid (produced by Nippon Kayaku Co., Ltd., tradename: R-551), 60 parts of an acylate having carboxyl groups obtained by esterifying equimolar amounts of hexahydrophthalic anhydride and 2-hydroxyethyl acrylate, 10 parts of polybutadiene diacrylate [produced by Nisso Polybutadiene Co., Ltd., NISSOPB, TE-2000 (tradename)] and 5 parts of 2-ethylanthraquinone as a photosensitizer. Each obtained composition was coated on a soft steel plate the surface of which had been degreased with toluene and further polished with #240 sand paper, and set by irradiating with ultraviolet light from a high pressure mercury lamp (produced by Tokyo Shibaura Electric Co., Ltd., 2 KW). As Comparative Example, a composition similar to the above but excluding the novel organic phosphate was coated and set similarly. The results are given in Table 1 below.

TABLE 1

| | No. | Organophosphate | Setting Time[1] | Adhesion[2] |
|---|---|---|---|---|
| Application Example | 1 | That obtained in Ex. 1 | 2 | 100/100 |
| | 2 | That obtained in Ex. 2 | 3 | 100/100 |

TABLE 1-continued

| | No. | Organophosphate | Setting Time[1] | Adhesion[2] |
|---|---|---|---|---|
| | 3 | That obtained in Ex. 3 | 1 | 100/100 |
| Comparative Example | 1 | Containing no organophosphate | 1 | 20/100 |

Notes:
[1] Number of passing times when the surface is passed 8 cm beneath a high pressure mercury lamp at a rate of 5 m/min until it is hand-felt dried.
[2] Number of remaining small squares out of 100 by a checkerboard peel-off test (JIS K-5400) using an adhesive tape.

EXAMPLES 4–10 AND COMPARATIVE EXAMPLES 2–4

The respective components were formulated at the formulating ratios set forth in Table 2, mixed and then dissolved to obtain adhesives respectively. They are all liquid substances.

TABLE 2

| Formulating Component | Example 4 | 5 | 6 | 7 | 8 | 9 | 10 | Comparative Example 2 | 3 | 4 |
|---|---|---|---|---|---|---|---|---|---|---|
| [Polymeric Monomer, Component A] | | | | | | | | | | |
| 2,2-Bis(4-methacryloxydiethoxyphenyl)propane | 80 | 80 | 80 | | 50 | 80 | 80 | 80 | 80 | |
| Trimethylolpropane trimethacrylate | | | | | 25 | | | | | |
| 2-Hydroxyethyl methacrylate | 20 | 20 | 20 | 100 | 25 | 20 | 20 | 20 | 20 | 100 |
| [Phosphate, Component B] | | | | | | | | | | |
| Ester obtained in Example 1 | 0.5 | 2 | 5 | 10 | | | | | | |
| Ester obtained in Example 2 | | | | | 15 | 2 | 5 | | | |
| KAYAMA PM2* | | | | | | | | 0.5 | 5 | 10 |
| [Organic Peroxide, Component C] | | | | | | | | | | |
| Cumene hydroperoxide | 3 | 3 | 3 | 3 | 3 | 3 | 3 | 3 | 3 | 3 |
| [Polymerization Accelerator] | | | | | | | | | | |
| o-Sulfobenzoicimide | 1 | 1 | 1 | 1 | 1 | 1 | 1 | 1 | 1 | 1 |
| 1,2,3,4-Tetrahydroquinoline | 0.4 | 0.4 | 0.4 | 0.4 | 0.4 | 0.4 | 0.4 | 0.4 | 0.4 | 0.4 |
| Dextrin | 0.03 | 0.03 | 0.03 | 0.03 | 0.03 | 0.03 | 0.03 | 0.03 | 0.03 | 0.03 |

*Mixture of bis(2-hydroxyethyl methacrylate) phosphate and 2-hydroxyethyl methacrylate phosphate (produced by Nippon Kayaku Co., Ltd.; tradename: KAYAMA PM2).

The data set forth in Table 3 given hereinlater are data on skin toxicity (P.I.I., Primary Irritation Index) tested on the phosphates produced in the preceding examples and commercially available KAYAMA PM2.

The data set forth in Table 4 are data obtained when the respective setting compositions (adhesives) formulated at the formulating ratios set forth in Table 2 were coated, set and measured for adhesive force.

Testing Method

The testing method for obtaining data relating to this case is as follows:

P.I.I. (Primary Irritation Index)

Measurement of P.I.I. was conducted by Huntingdon Research Centre (Huntingdon Cambs., PE18 6ES, England).

Outline of Measuring Method

Six white rabbits shaved by hair clippers were used, and 0.5 ml of the test sample was applied to one site. Each rabbit was restrained, the test sample was applied to the site (the side-spinal part on the back) by a patch mode, and immediately the trunk part including the patch part was covered with an impermeable substance such as rubber, cloth etc. for 24 hours. Twenty-four hours later, the patch was removed, and the skin reaction appeared on the site was scored according to the skin reaction standard.

Seventy-two hours later, the skin reaction was again scored. Also, the abraded skin was treated similarly as with the healthy skin. Abrasion of the skin should be restricted to peel-off of the corneum, and care should be taken so as not to reach the dermis and cause bleeding.

Judgement was also conducted on the abraded skin 24 hours and 72 hours later. The small sum of the erythema and and eschar formed on the healthy skin and the abraded skin 24 hours and 72 hours later was added to the small sum of the edema formed, and the total was divided by 24 to obtain a score for each animal. Thereafter, the average score for the six animals was calculated. This value is that expressed as an average primary irritation score called P.I.I. (Primary Irritation Index).

| Skin Reaction Standard | Score |
|---|---|
| Erythema and Eschar Formation | |
| No erythema | 0 |
| Very slight erythema (barely perceptible) | 1 |
| Well-defined erythema | 2 |
| Moderate to severe erythema | 3 |
| Severe erythema (beet redness) to slight eschar formation (injuries in depth) | 4 |
| Edema Formation | |
| No edema | 0 |
| Very slight edema (barely perceptible) | 1 |
| Slight edema (edges of area well-defined by definite raising) | 2 |
| Moderate edema (raised approximately 1 millimeter) | 3 |
| Severe edema (raised more than 1 millimeter and extending beyond the area of exposure) | 4 |

For the above, reference is made to Draize, John H., Woodard, Geoffrey and Calvery, Herbert O., "Methods for the Study of Irritation and Toxicity of Substances Applied Topically to the Skin and Mucous Membranes", J. Pharm. & Exp. Ther., 82, 337 (1944).

Measurement of Adhesive Force

This measurement was conducted according to JIS K 6850 (Method of Testing Tensile Shear Bond Strength of Adhesives).

Test Piece: Iron plate of a size of 1.0×2.5×100 mm with a bonded area of 2.5 cm². 
Tensile Tester: Tensilon, manufactured by Toyo Baldwin Co., Ltd.
Pulling speed: 10 mm/min.
Setting conditions: 120° C.×1 hour

TABLE 3

| Phosphate | P.I.I. |
| --- | --- |
| Ester obtained in Example 1 | 1.0 |
| Ester obtained in Example 2 | 0.7 |
| KAYAMA PM2*[1] | 3.3 |

*[1]KAYAMA PM2: Mixture of bis(2-hydroxyethyl methacrylate) phosphate and 2-hydroxyethyl methacrylate phosphate (produced by Nippon Kayaku Co., Ltd.).

TABLE 4

| | Example | | | | | | |
| --- | --- | --- | --- | --- | --- | --- | --- |
| | 4 | 5 | 6 | 7 | 8 | 9 | 10 |
| Adhesive Force (kg/cm$^2$) | 286 | 284 | 220 | 172 | 206 | 253 | 212 |

| | Comparative Example | | |
| --- | --- | --- | --- |
| | 2 | 3 | 4 |
| Adhesive Force (kg/cm$^2$) | 201 | 164 | 162 |

What is claimed is:

1. An adhesive which is characterized by comprising an anaerobically polymerizable monomer (A), a phosphate of the following formula:

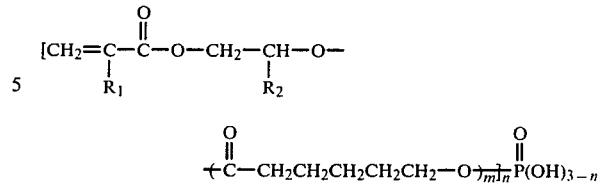

wherein $R_1$ and $R_2$ each represents H or $CH_3$, m is a numeral of 1-5 and n is a numeral of 1-2 (B) and an organic peroxide (C).

2. The adhesive according to claim 1 which contains 0.05-30 parts by weight of the component (B) per 100 parts by weight of the component (A) and 0.2-3 parts by weight of the component (C) per 100 parts by weight of the total of the component (A) and the component (B).

3. The adhesive according to claim 2 wherein the anaerobically polymerizable monomer (A) is one or more compounds selected from 2-hydroxyethyl methacrylate, 2-hydroxypropyl methacrylate, 2-hydroxyethyl acrylate, polyethylene glycol dimethacrylate, trimethylolpropane trimethacrylate, 2,2-bis(4-methacryloxydiethoxyphenyl)propane, 2,2-bis(4-methacryloxytriethoxyphenyl)propane.

4. The adhesive according to claim 1, 2 or 3 wherein the phosphate (B) is a phosphate wherein $R_1$ is $CH_3$, $R_2$ is H and m is a value of 1-2.

* * * * *